(12) United States Patent
Wolpensinger et al.

(10) Patent No.: US 11,110,420 B2
(45) Date of Patent: Sep. 7, 2021

(54) FLUIDIZED BED SYSTEM

(71) Applicant: Hüttlin GmbH, Schopfheim (DE)

(72) Inventors: Bernd Wolpensinger, Rheinfelden (DE); Christian Karl Paasche, Bad Saeckingen (DE); Marc Michaelis, Loerrach (DE); Matthias Boerner, Schopfheim (DE); Norbert Zerrer, Schopfheim (DE)

(73) Assignee: Hüttlin GmbH, Schopfheim (DE)

( * ) Notice: Subject to any disclaimer, the term of this patent is extended or adjusted under 35 U.S.C. 154(b) by 151 days.

(21) Appl. No.: 16/334,089

(22) PCT Filed: Jul. 19, 2017

(86) PCT No.: PCT/EP2017/068259
§ 371 (c)(1),
(2) Date: Mar. 18, 2019

(87) PCT Pub. No.: WO2018/054576
PCT Pub. Date: Mar. 29, 2018

(65) Prior Publication Data
US 2019/0358600 A1  Nov. 28, 2019

(30) Foreign Application Priority Data
Sep. 21, 2016  (DE) .................. 10 2016 218 085.1

(51) Int. Cl.
| | | |
|---|---|---|
| *B01J 2/10* | (2006.01) | |
| *B01J 2/16* | (2006.01) | |
| *A61K 9/16* | (2006.01) | |

(52) U.S. Cl.
CPC ............... *B01J 2/16* (2013.01); *A61K 9/1682* (2013.01)

(58) Field of Classification Search
CPC ................................. B01J 2/16; A61K 9/1682
See application file for complete search history.

(56) References Cited

U.S. PATENT DOCUMENTS

| | | | | |
|---|---|---|---|---|
| 6,058,624 A | * | 5/2000 | Bach ..................... | B01D 1/18 34/374 |
| 7,908,765 B2 | * | 3/2011 | Waldron ................. | B01J 2/10 34/138 |

(Continued)

FOREIGN PATENT DOCUMENTS

| | | |
|---|---|---|
| CH | 686343 | 3/1996 |
| CN | 1677067 A | 10/2005 |

(Continued)

OTHER PUBLICATIONS

International Search Report for Application No. PCT/EP2017/068259 dated Nov. 7, 2017 (English Translation, 3 pages).

(Continued)

*Primary Examiner* — Joseph S Del Sole
*Assistant Examiner* — Jamel M Nelson
(74) *Attorney, Agent, or Firm* — Michael Best & Friedrich LLP

(57) ABSTRACT

The invention relates to a fluidised bed system (1) comprising a plurality of granulation units (2), arranged so as to be functionally parallel, for producing pharmaceutical granules, each granulation unit (2) comprising: a fluidised bed container (3), an inlet (4) and an outlet (5) on said fluidised bed container (3), a fluid supply (6) and a fluid discharge (7) on said fluidised bed container (3), and at least one injection nozzle (8) for injecting a processing substance into the fluidised bed container (3), as well as a control unit for adjusting processing conditions within each granulation unit (2).

14 Claims, 8 Drawing Sheets

(56) References Cited

U.S. PATENT DOCUMENTS

| | | | | |
|---|---|---|---|---|
| 2003/0000228 A1* | 1/2003 | Leuenberger | ............ | F26B 3/08 62/64 |
| 2003/0012873 A1 | 1/2003 | Hirono et al. | | |
| 2016/0265843 A1 | 9/2016 | Bohle et al. | | |

FOREIGN PATENT DOCUMENTS

| | | | | |
|---|---|---|---|---|
| CN | 101303252 A | 11/2008 | | |
| CN | 101365410 A | 2/2009 | | |
| CN | 102573757 A | 7/2012 | | |
| CN | 104507442 A | 4/2015 | | |
| DE | 102013102133 | 9/2014 | | |
| DE | 102014103661 | 9/2015 | | |
| GB | 2269354 A | 2/1994 | | |
| JP | 2004290741 | 10/2004 | | |
| WO | 03033126 | 4/2003 | | |
| WO | WO-03033126 A1 * | 4/2003 | .............. | A23P 20/15 |

OTHER PUBLICATIONS

English Translation of Chinese Patent Office Action and Search Report for Application No. 201880085419.8 dated May 6, 2021 (8 pages).

* cited by examiner

Fig. 4
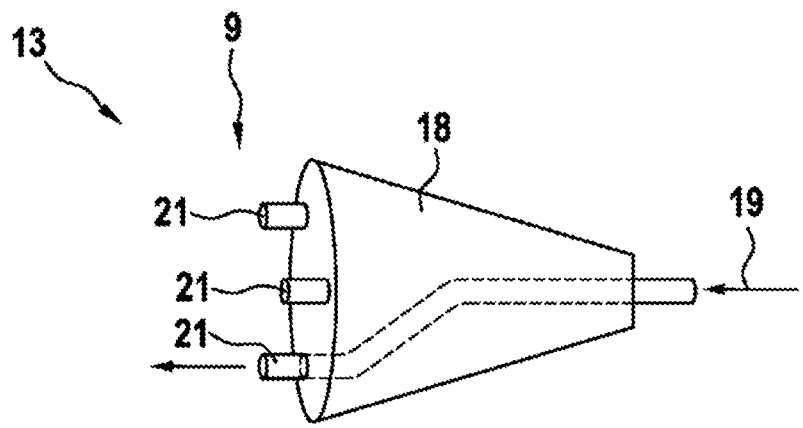
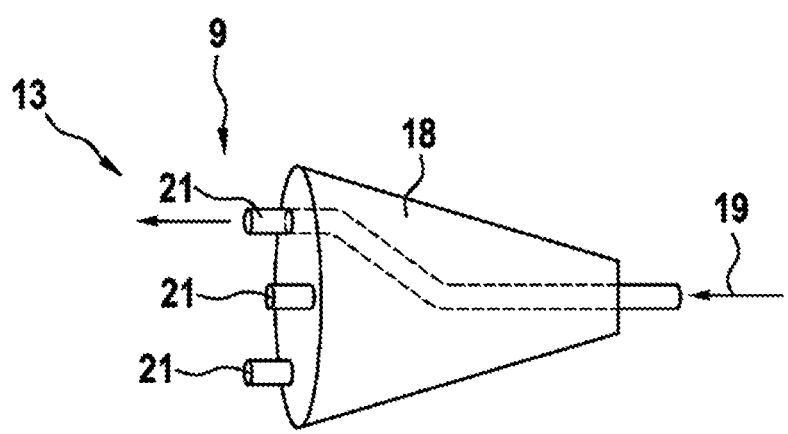
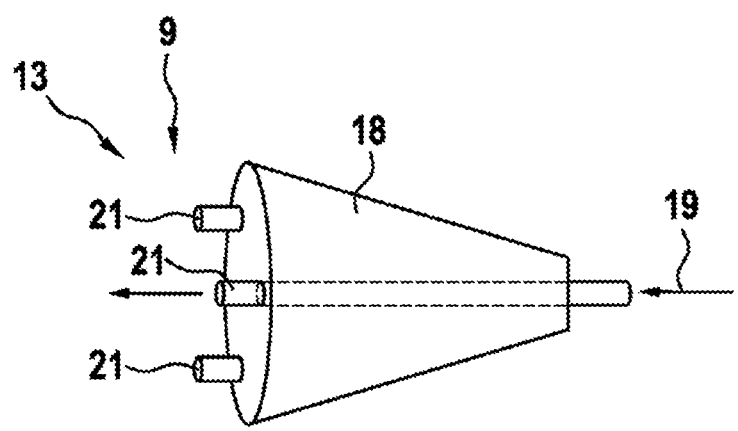

FLUIDIZED BED SYSTEM

BACKGROUND OF THE INVENTION

The invention relates to a fluidized bed system or installation. In particular, the invention relates to a fluidized bed granulation installation. The fluidized bed installation or the fluidized bed granulation installation are suitable in particular for processing pharmaceutical powders.

The processing of pharmaceutical powders in a fluidized bed is known from the prior art. This includes in particular the processes of drying, coating and granulation. At present, systems with extruder and downstream fluidized bed dryers are preferably used for continuously operated pharmaceutical wet granulation units. A disadvantage of such systems is the modified granule properties resulting from the greater compaction in the extruder. Wet granulation of pharmaceutical powders in the fluidized bed installation is known from batch-operated systems. However, satisfactory, fully automated, continuous or semicontinuous parallel operation of these systems has not hitherto been possible. In particular, no solution is known or accepted in pharmaceutical production which ensures continuous granulation in such a system and automated or partially automated intermediate cleaning of individual granulation units. Continuously operating fluidized bed granulation apparatuses are known from chemical production and/or food production which are constructed as a channel with or without weirs, or with classifying or non-classifying discharge. However, these systems are not accepted either in the pharmaceutical industry or by the licensing authorities. In addition, the pharmaceutical industry has not hitherto offered suitable process control or integration of higher-level overall control of the fluidized bed granulation installation into an entire production line, or the possibility of continuous or semicontinuous granulation and coating in parallel operation.

Examples of fluidized bed drying installations with a plurality of fluidized bed chambers are disclosed in U.S. Pat. No. 7,908,765 B2, DE 10 2013 102 133 A1 and DE 10 2014 103 661 A1.

SUMMARY OF THE INVENTION

The fluidized bed installation according to the invention allows fully automated granulation and drying of pharmaceutical powders. The fluidized bed installation according to the invention comprises a plurality of granulation units arranged functionally in parallel. In this respect, each granulation unit has to be individually loaded via an inlet and emptied via an outlet. The granulation unit preferably comprises an opening via which the inlet and outlet are embodied. To this end, each granulation unit comprises a fluidized bed tank, and an inlet and an outlet, which are each arranged on the fluidized bed tank. Moreover, each granulation unit comprises a fluid inflow and a fluid outflow, which are likewise arranged in each case on the fluidized bed tank. A working fluid, in particular air, may be introduced via the fluid inflow into the fluidized bed tank, where the fluid, in particular the working air, mixes with a pulverulent solid introducible via the inlet. The fluid may be removed from the fluidized bed tank via the fluid outflow, while the powder or the finished product may be removed from the fluidized bed tank via the outlet. Furthermore, the granulation unit comprises at least one spray nozzle for spraying a processing substance into the fluidized bed tank. The powder located within the fluidized bed tank may thus be coated or granulated with the processing substance. In this case, provision is made for a control unit to be provided, which is configured to adjust process conditions within each granulation unit. The process conditions may advantageously be adjusted on the basis of parameters, such as in particular temperature, pressure or moisture, of the fluid supplied via the fluid inflow. Moreover, the process conditions may advantageously be adjusted by the quantity of fluid supplied and/or by the quantity of powder or pulverulent solid supplied via the inlet. Adjustment of the process conditions within each granulation unit here proceeds advantageously independently of all the other granulation units. Through parallel operation automated in this way and adapted to the individual granulation units, granules may be produced at regular chronological intervals.

The fluidized bed tanks are advantageously of cylindrical construction and comprise a lid and a bottom. A side wall extends between the lid and the bottom. Provision is in this case advantageously made for the fluid inflow to be arranged in the bottom and the fluid outflow to be arranged in the lid, while the inlet and outlet are arranged in the side face. In this way, a solid, in particular a pulverulent solid, introduced via the inlet into the fluidized bed tank may be mixed with the working fluid which is introduced via the fluid inlet into the fluidized bed tank and which flows within the fluidized bed tank to the fluid outlet, whereby the in particular pulverulent solid to be processed adopts a fluid-like state. The side face preferably comprises one opening via which the inlet and outlet are embodied.

The dependent claims contain preferred further developments of the invention.

Provision is advantageously made for the fluidized bed installation to have an inlet line. The inlet line connects all the inlets of all the granulation units. The inlet line may also lead into a central distribution system. Provision is particularly advantageously made for the granulation units to be arranged in a ring, such that the inlet line constitutes a ring line. Alternatively, the granulation units are preferably arranged in linear manner in at least one row, such that the inlet line likewise extends in linear manner. Advantageously each inlet is connected to the inlet line via a valve, such that each fluidized bed tank of each granulation unit may be filled separately via the inlet line. Provision is made particularly advantageously for precisely one, in particular annular, inlet line to be present. Alternatively, the inlet line may preferably also comprise an individual line for each granulation unit. The inlet line is moreover preferably connected with a waste collection device, via which excess and/or defective material may be collected. Alternatively, each individual line may be directly connected in valve-free manner to the inlet of a waste collection device.

Furthermore, provision is preferably made for the fluidized bed installation to have an outlet line. The outlet line connects all the outlets of all the granulation units. Provision is in turn preferably made for the granulation units to be arranged in a ring, such that the outlet line is a ring line. The arrangement may alternatively also be linear, such that the outlet line likewise extends in a linear manner. Each outlet is advantageously connected to the outlet line via its own valve, such that individual granulation units may optionally be emptied. The outlet line is also advantageously connected with a waste collection device. In this way, excess material can be collected and preferably disposed of via the waste collection device. The waste collection device may be the same waste collection device as previously described. Provision is particularly advantageously made, both for the inlet line and for the outlet line, for said lines to be annular, wherein the lines may also have other shapes, in particular they may extend in a linear manner. In this respect, the inlet line and/or the outlet line may also take the form of ring segments. In a further particularly preferred embodiment, the granulation units are arranged in an annular manner, wherein the inlet line at least in part encloses the granulation units from outside while the outlet line, at least in the form of a ring segment, is arranged inside the annularly arranged granulation units. This ensures a highly space-saving construction. A linear arrangement of the granulation units provides good accessibility for each individual granulation unit within the fluidized bed installation. Simple manual cleanability may thus in particular also be achieved.

In one advantageous embodiment, the fluidized bed installation comprises a cleaning module. The cleaning module is operatively connected with each granulation unit. An annular or ring segment-shaped cleaning line is particularly advantageously present, which connects the fluidized bed tanks of all the granulation units. Each granulation unit may thus be cleaned by the cleaning module. Provision is in turn particularly advantageously made for valves to be present to connect each fluidized bed tank with the cleaning line. It is thus ensured that cleaning of one granulation unit may proceed independently of other granulation units. This in particular also makes it possible for one granulation unit to be cleaned while other granulation units continue to operate.

The cleaning module is particularly advantageously configured to perform cleaning with manual intervention. Such cleaning is also known as Wash in Place (WIP). Alternatively or additionally, the cleaning module is advantageously configured to perform cleaning without manual intervention. Such cleaning is also known as Clean in Place (CIP). The fluidized bed installation may thus be cleaned at least partly automatically by the cleaning module, wherein cleaning may affect just some of the plurality of granulation units. Production using the fluidized bed installation may thus be impaired only slightly or not at all by cleaning operations.

The fluidized bed installation preferably comprises at least one module inlet. The module inlet is connected with the inlets of all the granulation units. The above-described inlet line is particularly advantageously present, such that the module inlet is connected with the inlet line. The module inlet is drivable by the control unit. Thus, the control unit is a centralized entity not only for driving the individual granulation units, but also for driving the module inlet. The granulation process may thus take place safely and reliably within the granulation units, since all the preparatory work parameters are known.

The module inlet may in particular be a central distribution module and/or a switch and/or a ring line and/or a changeover valve and/or a buffer tank. The optimal quantity needed for one of the granulation units may thus always be provided and supplied to the granulation unit. Alternatively or in addition, the preparatory module may comprise an input mill and/or an input scale.

Provision may furthermore preferably be made for the fluidized bed installation to comprise at least one module outlet. The module outlet is connected with the outlets of all the granulation units. Particularly advantageously, the above-described outlet line is present, wherein the module outlet is connected with the outlet line. The module outlet is drivable by the control unit.

Finally, provision is preferably made for the spray nozzle to be arranged in a bottom and/or in a lid and/or in a side wall of the granulation unit. A plurality of spray nozzles are particularly advantageously present. A processing substance, in particular a granulation liquid, may be sprayed into the fluidized bed tank via the spray nozzles, such that the powder located within the fluidized bed tank may be granulated or otherwise processed, in particular by coating. This in particular enables the production of pharmaceutical agents. Particularly advantageously, a plurality of spray nozzles may be arranged, in particular at different locations within the granulation unit and/or the fluidized bed tank.

The invention additionally relates to a method for semi-continuous production, in particular of pharmaceutical granules within a fluidized bed installation. In this case, provision is made for individual granulation units of the fluidized bed installation to be individually and/or mutually independently operable. Moreover, provision is preferably made for the individual granulation units to be cleanable independently of operation of the other granulation units. This allows fluidized bed installations to operate without interruption.

BRIEF DESCRIPTION OF THE DRAWINGS

Exemplary embodiments of the invention are described in detail below with reference to the accompanying drawings, in which:

FIG. 4 shows a first alternative of a module inlet of a fluidized bed installation according to the exemplary embodiment of the invention.

DETAILED DESCRIPTION

Figure 1:
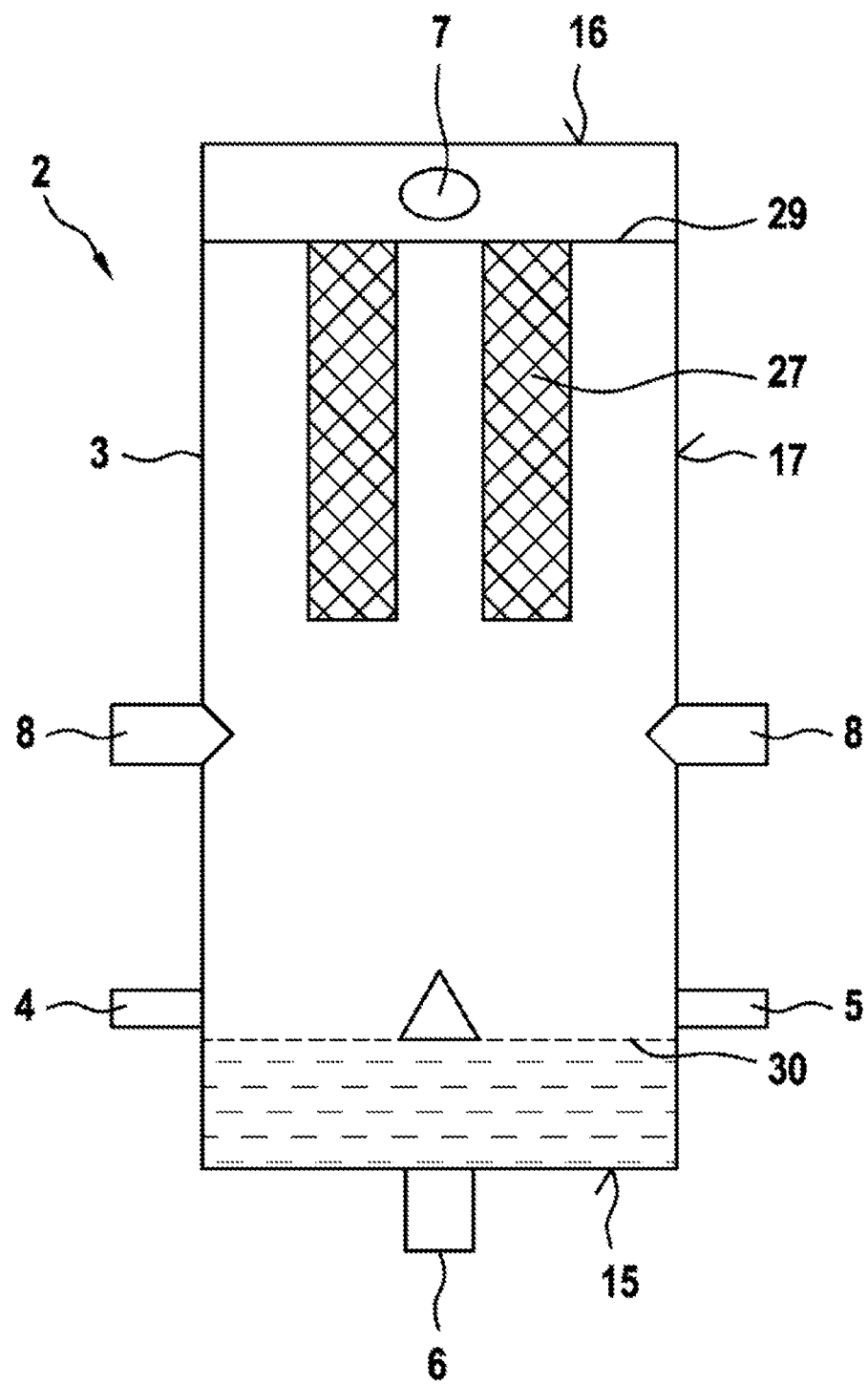
FIG. 1 shows a schematic depiction of a granulation unit of a fluidized bed installation according to one exemplary embodiment of the invention.

FIG. 1 shows a granulation unit 2 of a fluidized bed installation 1 (cf. FIGS. 2 and 3) according to one exemplary embodiment of the invention. A fluid, in particular a gas, particularly preferably air, is fed to the granulation unit 2 via an air treatment installation, not shown, with heat exchanger, filter and external air supply. Gas is fed into the granulation unit 2 via a fluid inflow 6, wherein the fluid inflow 6 is arranged in a bottom 15 of the granulation unit 2. A disk-shaped gas distributor plate 30 is in particular arranged above the bottom 15, which plate distributes the supplied air over a large area across the entire cross-section of the fluidized bed tank 3.

The bottom 15 is in particular is of circular construction and delimits a hollow-cylindrical fluidized bed tank 3. Moreover, the fluidized bed tank 3 is delimited by a likewise circular lid 16. Thus, side walls 17 of the fluidized bed tank 3 extend between the bottom 15 and the lid 16. The bottom 15 and lid 16 are in particular arranged parallel to one another.

A disk-shaped filter plate 29 is provided in parallel below the lid 16. This filter plate 29 comprises and supports at least one filter 27, which is arranged at a fluid outlet 7. The gas introduced via the fluid inlet 6 in the bottom 15 may thus be removed from the granulation unit 2 via the filter 27 and via the fluid outlet 7. In this way, a fluid stream, in particular a gas stream, may be generated within the fluidized bed tank 3. Furthermore, the granulation unit 2 comprises spray nozzles 8, which project in particular into the interior of the fluidized bed tank 3. FIG. 1 shows the spray nozzles as lateral spray (side spray) nozzles. Alternatively or in addition, spray nozzles 8 may be arranged within the bottom 15 (bottom spray) and/or within the lid 16 (top spray). The spray nozzles deliver a processing substance, in particular a granulation liquid, which is intended for use in the process within the fluidized bed tank 3. The space enclosed by the fluidized bed tank 3 between the bottom 15 and the lid 16, in particular between the gas distributor plate 30 and the filter 27, forms the process chamber, through which gas introduced via the fluid inlet 6 thus flows. The process chamber extends from a center axis of the fluidized bed tank 3 to the side wall 17 and is rotationally symmetrical, particularly advantageously cylindrical in structure. A pulverulent solid may be introduced into the process chamber via an inlet 4, which extends through the side wall 17. A finished product, in particular dry granules, may be removed from the fluidized bed tank 3 via an outlet 5, which likewise extends through the side wall 17. The pulverulent solid and the granules are preferably conveyed pneumatically into and out of the granulation unit by suction, or alternatively gravimetrically with suitable apparatus.

The gas flowing through the process chamber, which flows through the process chamber from the fluid inlet 6 present in the bottom 15 to the fluid outlet 7 present in the lid 16, sets the pulverulent solid introduced into the process chamber via the inlet 4 into fluid-like motion. In the process, intensive heat exchange and mass transfer take place, enabled by a very intensive mixing process. This mixing process also makes it possible to mix the fluidized powder located in the process chamber with a granulation liquid sprayed into the process chamber via the spray nozzles 8. Mixing of the fluidized powder with the sprayed-in granulation liquid enables a plurality of individual particles of the powder to agglomerate into particle collectives (agglomerates). Through the simultaneous intensive transfer of heat, a major part of the granulation liquid evaporates at the agglomerate surface and in part in the pores of the agglomerates, such that these dry. However some liquid does remain in the agglomerates, so enabling the individual particles to stick together. The resultant agglomerate collective is known as granules.

The granulation liquid may, as described above, be fed in different ways into the process chamber. For instance, top spray, bottom spray and side spray methods may in particular be used. The spray nozzles 8 advantageously comprise three-fluid nozzles.

The process of fluidized bed granulation within each granulation unit 2 is monitored in the feed air and exhaust air lines, which connect the fluid inlet 6 with an air supply and the fluid outlet 7 with air extraction, above and below the bottom 15, in the process chamber, and upstream and downstream of the filter 27 using measurement devices which are not shown. In this case, the measurement devices advantageously determine data which allow statements to be made about the gas mass flow rate between fluid inlet 6 and fluid outlet 7, about the humidity of the gas, about the temperature of the gas and of the solid, about a pressure drop within the bottom 15, which preferably takes the form of an air distributor bottom, and at the filter 27, and optionally about particle size distribution and about product moisture content. These data are transmitted to a control unit 12 (cf. FIG. 3) of the fluidized bed installation 1. Provision is here made for a control unit 12 to be used as a higher-level control for all granulation units 2 present. Corresponding actuators of the individual granulation units 2 may be influenced via the control unit 12, in order to operate the process in the individual granulation units 2 stably and reliably within specified process limits. To this end, valves for controlling material transport through the inlet 4 and the outlet 5, for controlling fluid flow, in particular gas flow, between fluid inlet 6 and fluid outlet 7, and for controlling a cleaning system, may be appropriately adjusted. The functionality of the cleaning system, in particular of a cleaning module 11, is described below with reference to FIG. 2.

Figure 2:
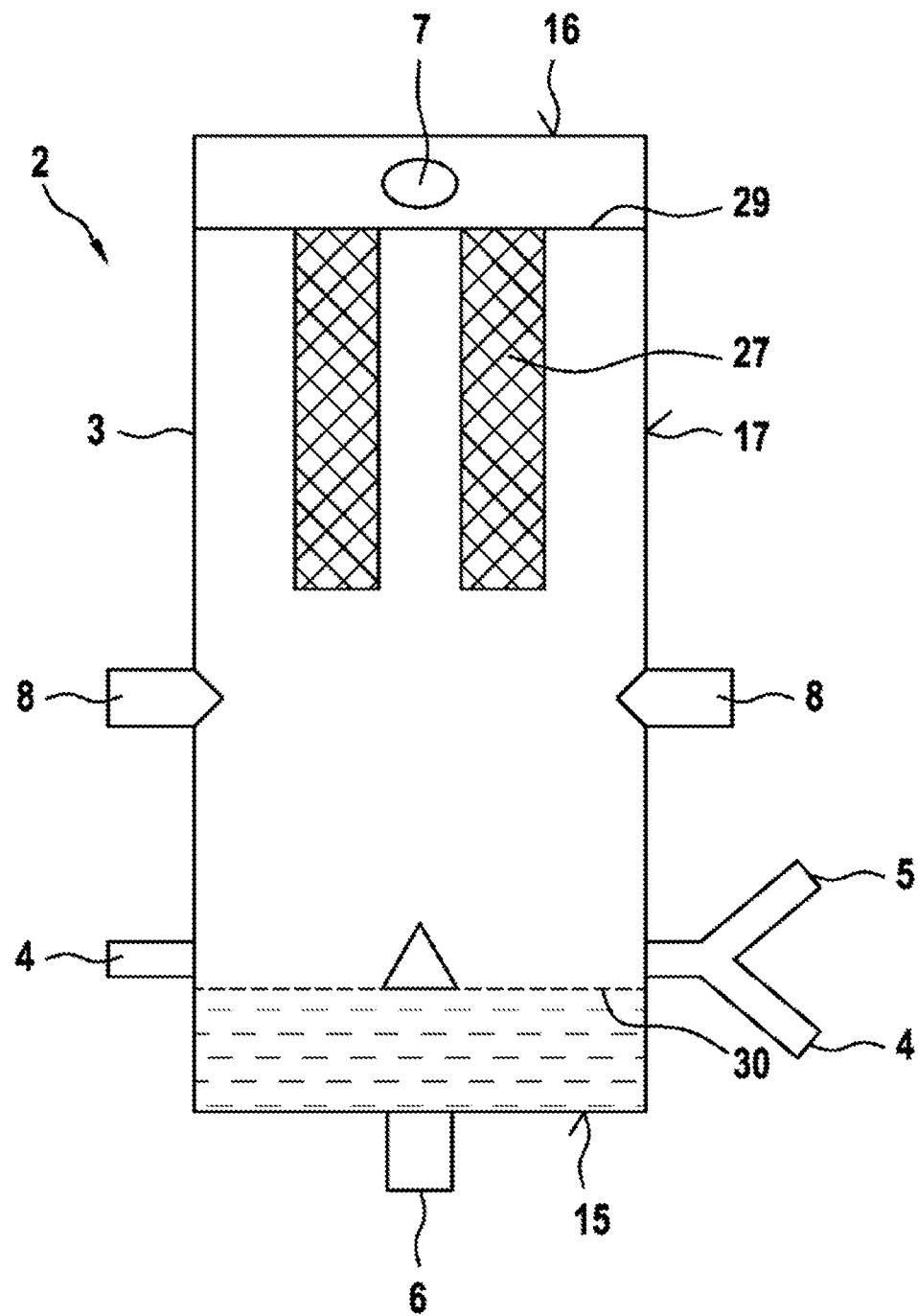
FIG. 2 shows a schematic depiction of an alternative granulation unit of a fluidized bed installation according to the exemplary embodiment of the invention.

FIG. 2 shows an alternative embodiment of the granulation units 2 of the fluidized bed installation 1. The alternative embodiment is identical to the embodiment shown in FIG. 1, the only difference between FIG. 1 and FIG. 2 being in relation to the inlet 4 and the outlet 5. In FIG. 1 each side face 3 has its own opening, for the inlet 4 and the outlet 5. In the alternative shown in FIG. 2, just one opening is present within the side face 3, wherein the inlet 4 and outlet 5 are embodied by this common opening in the side face 3.

Figure 3:
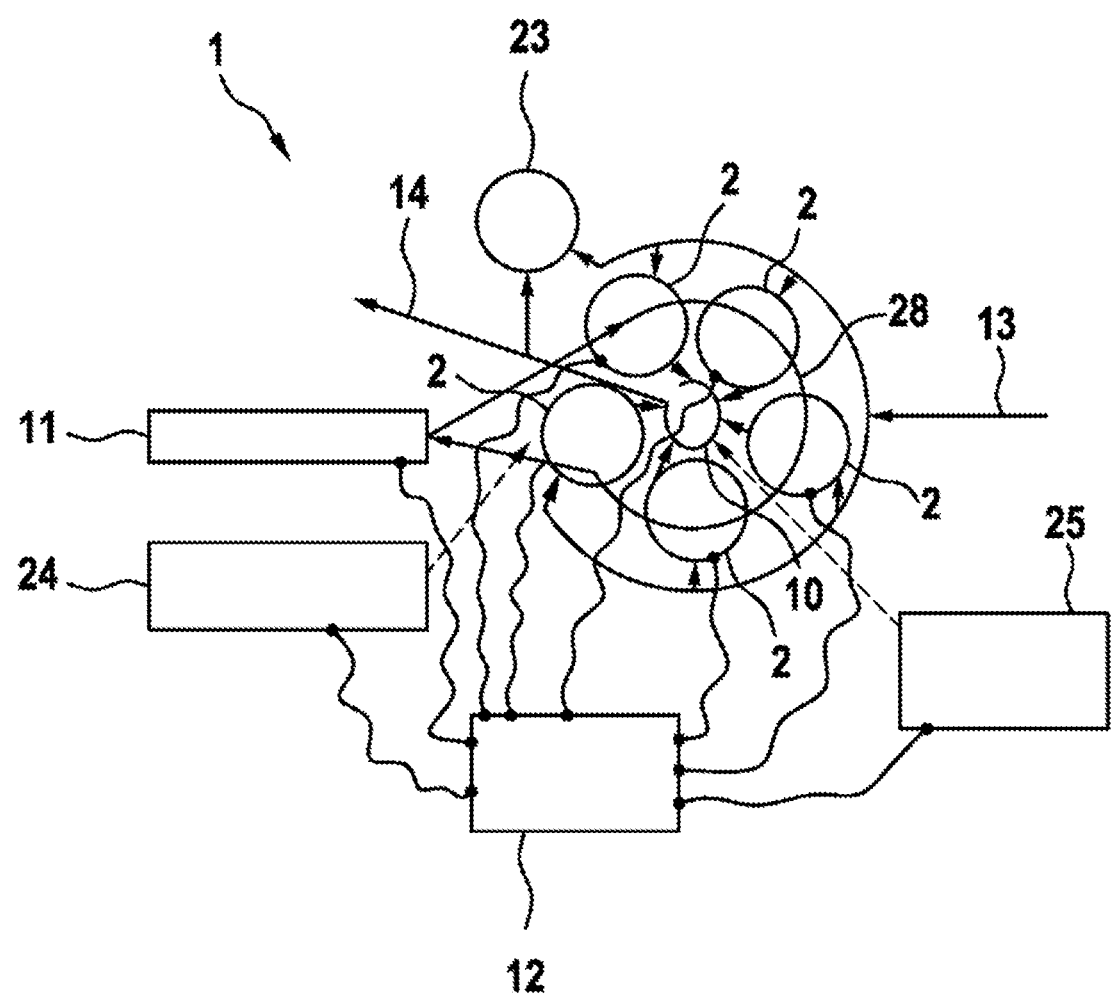
FIG. 3 shows a schematic depiction of a fluidized bed installation according to a second alternative of the exemplary embodiment of the invention.

FIG. 3 shows a first alternative of a fluidized bed installation 1 according to the exemplary embodiment of the invention. The fluidized bed installation 1 comprises five granulation units 2. The fluidized bed installation 1 in particular comprises at least two, particularly advantageously up to ten or more individual granulation units 2. All the granulation units 2 may be operated in parallel. In this respect, provision is preferably made for at least one granulation unit to remain in standby mode until activated. Provision is furthermore made for the granulation installation 1 to comprise a facility for disposing of reject material. Such a waste collection device 23 advantageously serves in collecting both reject material from among the pulverulent solid to be introduced into the granulation units 2 and from among the finished granules.

The individual granulation units 2 preferably comprise a common air supply 24. The air supply 24 is connected with all the fluid inlets 6 of the granulation units 2. Provision is however preferably made for a quantity and/or a moisture content and/or an inlet temperature of the gas flowing through the fluid inlet 6 to be individually adjustable for each granulation unit 2 via the control unit 12. Alternatively, each granulation unit 2 may have its own air supply 24.

The fluidized bed installation 1 further comprises a cleaning module 11. The cleaning module in particular allows cleaning without manual intervention (Clean in Place, CIP) or alternatively cleaning with manual intervention (Wash in Place, WIP). The cleaning module is connected to each granulation unit 2 via a cleaning line 28 for fully automated cleaning. The connection is advantageously permanent, but may alternatively also be produced merely for cleaning purposes. The cleaning line 28 is preferably connected via valves to each individual granulation unit 2 and, as required and in selectively drivable manner, ideally supplies with a cleaning medium one or more cleaning nozzles which are advantageously arranged in the side wall 17 and/or in the fluid inlet 6 and/or in the fluid outlet 7 and/or in the lid 16 and/or in the filter plate 29 and/or in the bottom 15 and/or in the inlet 4 and/or in the outlet 5 and/or in the feed line 9 and/or in the outlet line 10 and/or in the module inlet 13 and/or in the module outlet 14 and/or in the overall inlet 19, wherein these valves may be driven by the control unit 12. Each granulation unit 2 may thus be cleaned individually by the control unit 12, wherein operation of the remaining granulation units 2 is not impaired.

The fluidized bed installation 1 further comprises a line 9, which takes the form of a ring segment or is annular. The inlet line 9 encloses the annularly arranged granulation units 2 and connects all the inlets of the granulation units 2. In this respect, provision is made for each inlet 4 of a granulation unit 2 to be connected with the inlet line 9 via a valve drivable by the control unit 12. The control unit 12 is thus able to control which granulation unit 2 is to be supplied with a pulverulent solid. The inlet line 9 is moreover connected with the waste collection device 23, so as to transfer unsuitable material to the waste collection device 23. Here too, provision is made for a valve to be present between waste collection device 23 and inlet line 9, wherein this valve is controllable by the control device 12. Finally, provision is made for the inlet line 9 to be connected with a module inlet 13. The inlet line 9 may be filled with a material, in particular with a pulverulent solid, via the module inlet 13.

The fluidized bed installation 1 further comprises an outlet line 10. The outlet line 10 takes the form of a ring segment and is enclosed by the annularly arranged granulation units 2. Provision is here made for the outlet line 10 to connect the outlets 5 of all the granulation units 2. This connection is achieved in each case via a dedicated valve, wherein each valve may be driven by the control device 12 independently of every other valve. The outlet line 10 is moreover connected with the waste collection device 23, in order to dispose of reject material from among the granules produced in the granulation units 2. Here too, a valve is preferably present which is controllable by the control unit 12. Finally, the outlet line 10 is connected with a module outlet 14. Here a valve is in turn preferably present, wherein the valve is controllable by the control unit 12.

With the control unit 12, the fluidized bed installation 1 comprises a higher-level overall control means which, in addition to the plurality of granulation units 2, in particular also drives the preparatory module 13 and the cleaning module 11.

A transport air supply 25 is moreover preferably present. The transport air supply 25 allows pneumatic removal of the granules from the granulation units 2 by sucking the granules into the outlet line 10. The transport air supply 25 serves for this purpose. The transport air supply 25 moreover ensures that the granules can be transported to the module outlet 14.

How the fluidized bed installation 1 may be used is described below, by way of example:

The air supply 24 pneumatically fills the granulation units 2 with pulverulent solid in series, one after the other at an interval of at least ten to 600 seconds or more. In this connection, the air stream makes it possible to generate suction within each granulation unit 2, said suction enabling the pulverulent solid to be sucked into the fluidized bed tank 3. Alternatively, the granulation units 2 may be filled gravimetrically. As soon as the filling operation for one individual granulation unit 2 is complete, fluidized bed granulation commences in that granulation unit 2. Emptying of the granules from the granulation units 2 likewise proceeds pneumatically with the transport air supply 25, in that the granulation unit does not generate any more suction but rather the transport air supply 25 generates suction in the outlet line 10. Alternatively, emptying may also proceed gravimetrically. Emptying takes place in series with the same time interval as filling, wherein the sequence and time interval for emptying the individual granulation units 2 corresponds to the filling sequence. Each granulation unit 2 is preferably refilled with pulverulent solid directly after emptying. The emptying time may alternatively be determined by the achievement of a termination criterion (temperatures or humidity in the process chamber) of the granulation and drying process.

When a granulation unit 2 has been filled and emptied again once, this granulation unit 2 has gone through one cycle. Depending on the material, each granulation unit 2 may be operated over a number of cycles without cleaning. Once a predefined maximum number of cycles has been reached, the control device 12 initiates fully automated cleaning or pre-cleaning of the respective granulation unit 2 using the cleaning module 11. Once cleaning or pre-cleaning is complete, the granulation unit 2 may be brought directly back into operation or given a final manual clean if necessary. The cleaning process using the cleaning module 11 runs in such a way that the other granulation units 2 may continue to be operated during it.

The higher-level overall control means in the form the control unit 12 controls the air supply 24 for the process gas, i.e. the fluid which is supplied to each granulation unit 2 via the fluid inflow 6, and the transport air supply 25. Furthermore, the overall control means in the form of the control unit 12 controls all the valves for product transport and/or material transport which are connected with the inlet line 9 and/or the outlet line 10. Finally, the overall control means in the form of the control unit 12 controls the cleaning module 11 and all the actuators which influence the process of fluidized bed granulation in the individual granulation units 2. This makes it possible for the process parameters to be kept stably and reliably within specified process limits, whereby fluidized bed granulation proceeds very safely and reliably. Furthermore, the overall control means in the form of the control unit 12 monitors the fluidized bed installation 1 in such a way that all measurement data from the sensors located in the granulation units 2 are recorded and evaluated. Moreover, the measurement data may be displayed to an operator on a human/machine interface. In this way, any technical problems which may occur, which could potentially cause the process to suffer technical malfunctions or quality fluctuations, can be quickly identified. In particular, the time profile of the pressure drop across the gas distributor plate 30 of each granulation unit 2 or across the filter 27 of each granulation unit 2 may be mentioned in this respect. If the increase over time of this parameter is recorded and identified as problematic, the control unit 12 may decide independently which granulation unit 2 should be cleaned automatically next and/or output a report to the user stating that corresponding cleaning needs to be performed. Monitoring of the rate of spraying of the granulation liquid by means of the spray nozzles 8 may also be used as an indicator of the condition of the spray nozzles 8 or of the lines downstream thereof. The granulation installation 1 is thus capable of autonomously monitoring its technical condition and of optimizing it, so minimizing downtime.

FIG. 4 is a schematic diagram of a first alternative of a module inlet 13. In this case, the module inlet 13 takes the form of a switch 18. In the example shown in FIG. 4, the switch 18 has a plurality of individual outlets 21, which together produce the inlet line 9. Each individual outlet 21 may be separately connected with an overall inlet 19. FIG. 4 shows 3 different ways in which each individual outlet 21 may be connected with the overall inlet 19. The inlet line 9 thus comprises a plurality of individual lines, which connect each individual outlet 21 with a granulation unit 2.

Figure 5:
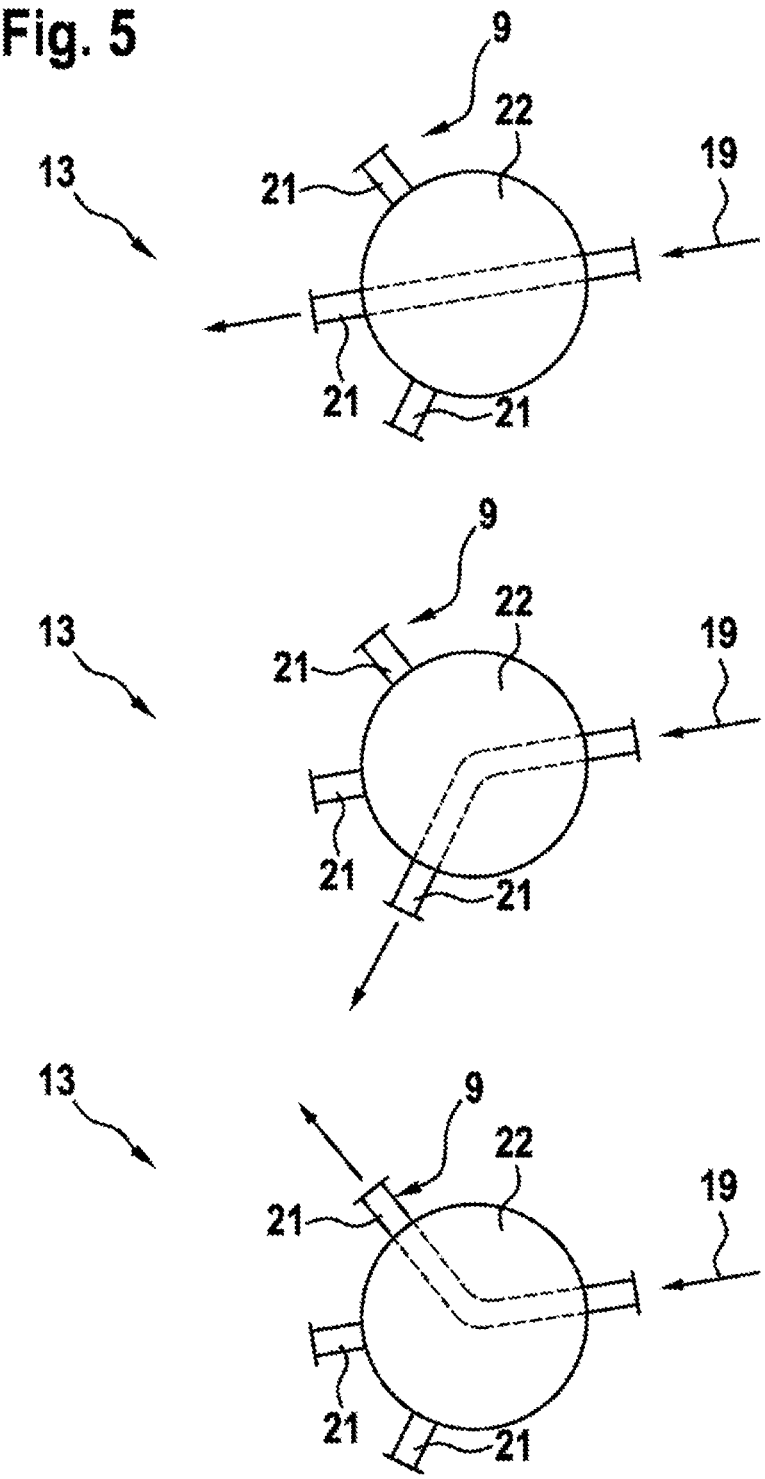
FIG. 5 shows a second alternative of a module inlet of a fluidized bed installation according to the exemplary embodiment of the invention.
Figure 6:
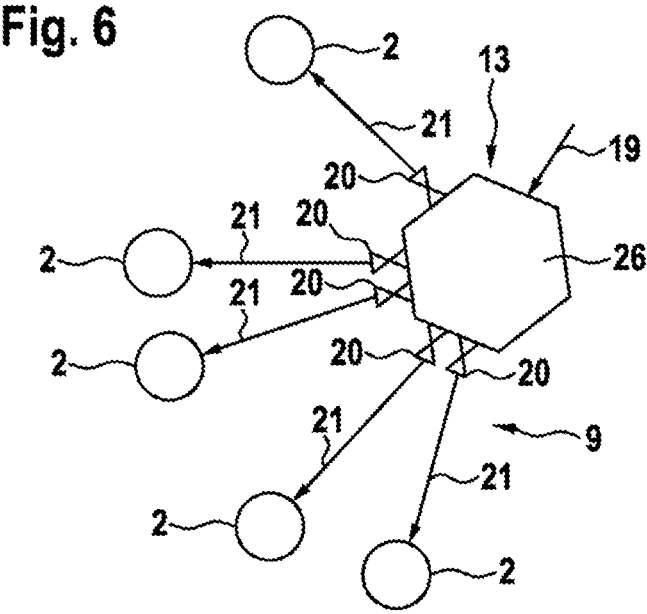
FIG. 6 shows a third alternative of a module inlet of a fluidized bed installation according to the exemplary embodiment of the invention.

FIG. 5 is a schematic diagram of a second alternative of the module inlet 13. In this case, the module inlet 13 takes the form of a changeover unit 22. As is already the case in the example shown in FIG. 4, a plurality of individual outlets 21 is again present, wherein the individual outlets 21 jointly form the inlet line 9. Provision is thus again preferably made for each individual outlet 21 to be connected separately in each case with one granulation unit 2. Each individual outlet 21 may be individually connected to the overall inlet 19 by the changeover unit 22. FIG. 6 is a schematic diagram of a third alternative of the module inlet 13. In this case, the module inlet 13 comprises a central distributor 26, which has a plurality of individual valves 20. Each individual valve 20 is connected with the overall inlet 19 via the central distributor 26. Each individual valve 20 controls an individual outlet 21, wherein each individual outlet 21 is again connected with precisely one granulation unit 2. The associated granulation units 2 may thus be connected to the overall inlet 19 by driving each individual valve 20.

Figure 7:
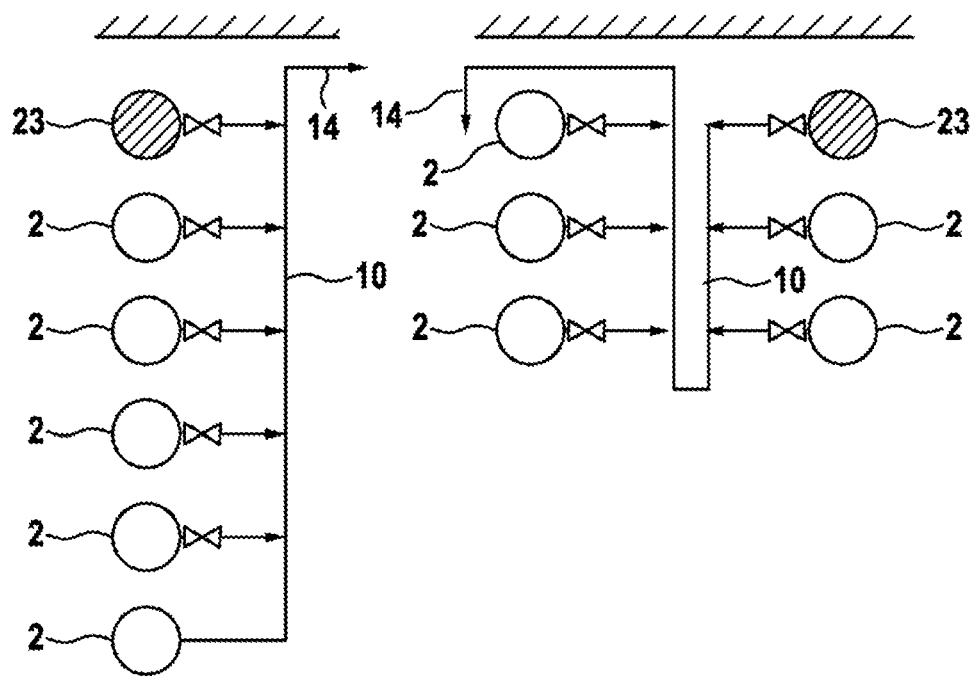
FIG. 7 shows alternatives of a module inlet of a fluidized bed installation according to the exemplary embodiment of the invention.

FIG. 7 is a schematic diagram of two preferred alternatives of a module outlet 14 of the fluidized bed installation 1. It is for instance possible, on the one hand, to use an outlet line 10 extending in linear manner, which is connected to the module outlet 14. This is advantageous in particular when the granulation units 2 and in particular also any waste collection device 23 that may be present are arranged in series, i.e. in particular in one row. Alternatively, the outlet line 10 as shown in FIG. 7 may extend in a U shape, if the granulation units 2 and in particular also any waste collection device 23 that may be present are arranged in two or more rows. The module outlet is again preferably connected with the outlet line 10.

Figure 8:
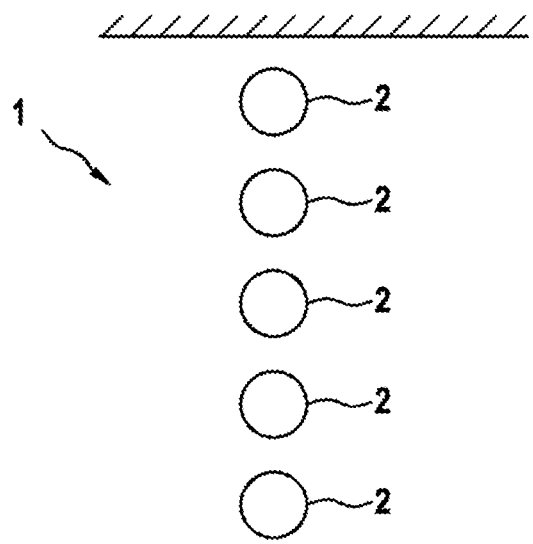
FIG. 8 shows a first alternative arrangement of the granulation units of the fluidized bed installation according to the exemplary embodiment of the invention.
Figure 9:
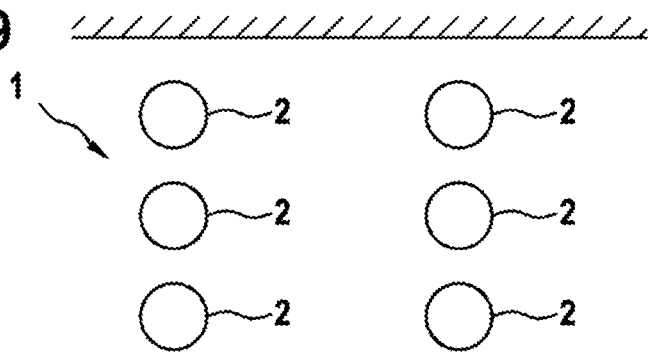
FIG. 9 shows a second alternative arrangement of the granulation units of the fluidized bed installation according to the exemplary embodiment of the invention.
Figure 10:
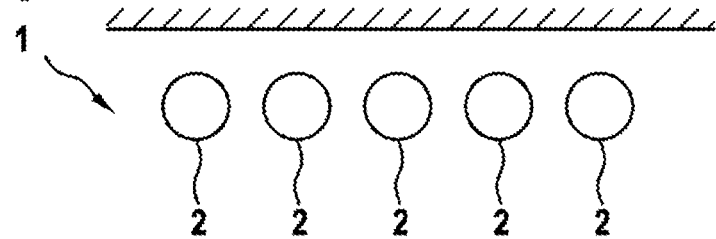
FIG. 10 shows a third alternative arrangement of the granulation units of the fluidized bed installation according to the exemplary embodiment of the invention.

FIGS. 8 to 10 preferably show alternative examples of arrangements to the annular arrangement of granulation units 2 shown in FIG. 3. In FIGS. 8 to 10, for instance, fluidized bed installations 1 are merely represented by the granulation units 2. The other components shown in FIG. 3 are not shown in FIGS. 8 to 10 for greater clarity.

FIG. 8, for instance, shows a schematic arrangement of the fluidized bed installation 1 in which the granulation units 2 are arranged in a column. This in particular has the advantage that each granulation unit 2 is simply accessible from outside, such that it may be easily reached by a user for maintenance and/or manual cleaning. In FIG. 9 the granulation units 2 form two columns extending in parallel. Finally, FIG. 10 shows the granulation units 2 arranged in a row. The above-described advantages with regard to accessibility and simplicity of maintenance and/or manual cleaning are also achieved in this case. It is likewise possible to arrange a plurality of granulation units 2 in parallel rows.

Figure 11:
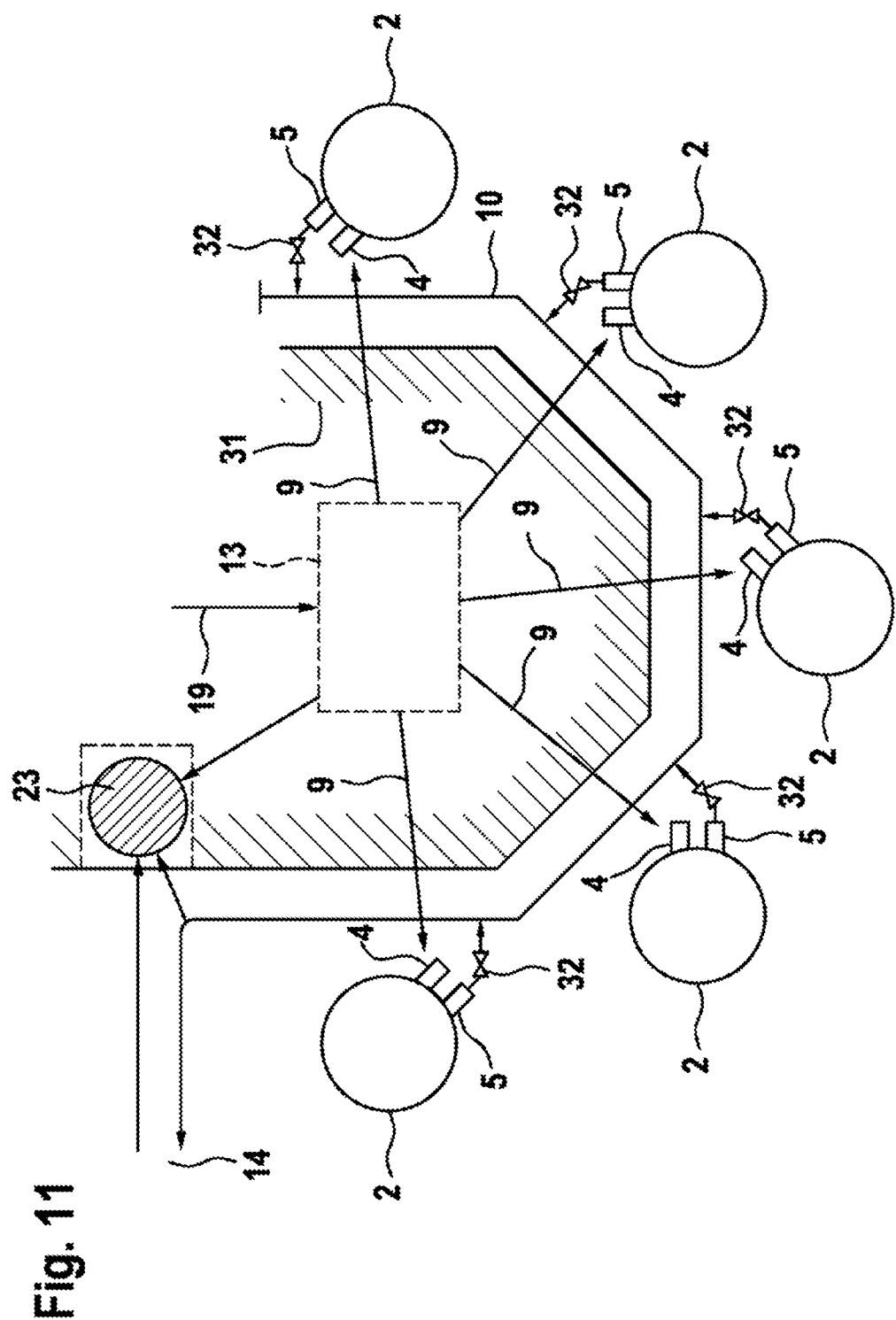
FIG. 11 shows a further schematic depiction of a part of the fluidized bed installation according to the exemplary embodiment of the invention.

FIG. 11 shows a further alternative of a fluidized bed installation 1 according to the exemplary embodiment of the invention. The granulation units 2 are arranged in a semicircle on a polygonal, basically semicircular interconnection wall 31. The inlet 4 and outlet 5 are oriented towards the interconnection wall 31. The powder inlet 4 of each granulation unit 2 is connected with its own inlet line 9 through the interconnection wall 31. Each inlet line 9 is connected with the module inlet 13. The overall powder inlet 19 is connected with the module inlet 13. The outlet 5 of each granulation unit is connected with the outlet line 10, wherein a shut-off valve 32 is here advantageously interposed for carrying out maintenance work as required on the outlet 5 of the granulation unit 2 while the other granulation units 2 are in operation and product is optionally being transported by the outlet line 10 The outlet line 10 transports the product to the module outlet 14. The waste collection device 23 is connected both via the inlet line 9 to the module inlet 13 and alternatively to the outlet line 10, ideally to the module outlet 14. Control unit 12, air supplies 24 and 25 and cleaning system 11 are not shown for greater clarity.

The fluidized bed installation 1 has the following advantages:

- no scaling up from laboratory tests to production processes, since the installation can be used for both purposes,
- just one inlet for a plurality of pharmaceutical powders to the module inlet 13,
- 100 percent traceability for each batch,
- no cross-contamination between the individual batches, since the granulation units 2 are operated completely separately and independently of one another,
- individual granulation units 2 are automatically cleanable during operation of the other granulation units 2, without the fluidized bed installation 1 having to be opened; alternatively, the granulation units 2 may be pre-cleaned, such that manual after-cleaning is required; in any event, cleaning and/or pre-cleaning take place during ongoing operation of the other granulation units 2,
- fluid supply, in particular air supply, of each granulation unit 2 is individually and independently controllable; dedicated parameters may be set for each granulation unit 2, such as in particular air quantity, air humidity and air temperature,
- supply of the individual granulation units 2, and of the reject material receptacles, preferably via individual ring lines, wherein the ring lines may be annular or take the form of ring segments,
- possibility of purging before and after fluidized bed granulation,
- the described inlet line 9 and the outlet line 10 reduce the number of valves required and increase process flexibility,
- various possibilities for spraying in processing substances, in particular granulating liquids: top spray, bottom spray, side spray,
- integration into an open-loop control concept and/or closed-loop control concept of the granulation units 2, which means
    - higher-level control means for integration of the individual granulation units 2 into the fluidized bed installation 1,
    - embodiment of closed-loop control using higher-level control means for the individual granulation units 2.
- an efficient, coordinated process analytical technology concept (PAT concept) in all the granulation units 2
- Continuous Process Verification (CVP)
- Soft Sensor Modeling
- PAT (Process Analytical Technology)

SPC (Statistical Process Control) by means of MVDA (multivariate data analysis) and univariate data analysis database system for managing data, collecting data, and evaluating data automatic identification of possible technical problems that may occur with the individual granulation units 2 and reporting to a user; display of recommendations and advantageously independent implementation of measures, in particular cleaning, to prevent more serious problems, minimization of downtime and quantity of scrap material, development and production on one installation, test programs carried out automatically (DoE, etc.) across a complete fluidized bed calculation process as per user specifications various formulations various filling quantities various operating parameters.

What is claimed is:

1. A fluidized bed installation (1) comprising
(i) a plurality of granulation units (2) for the production of pharmaceutical granules, wherein each granulation unit (2) comprises:
a fluidized bed tank (3),
an inlet (4) and an outlet (5) on the fluidized bed tank (3), the inlet (4) configured to deliver a pulverulent solid to the fluidized bed tank (3) and the outlet (5) configured to remove a finished product from the fluidized bed tank (3),
a fluid inflow (6) and a fluid outflow (7) on the fluidized bed tank (3), the fluid inflow (6) configured to deliver a working fluid to fluidized bed tank (3) and the fluid outflow (7) configured to remove the working fluid from the fluidized bed tank (3), and
at least one spray nozzle (8) for spraying a processing substance into the fluidized bed tank (3),
(ii) an inlet line (19) configured to deliver the pulverulent solid to the granulation units (2),
(iii) an outlet line (10) configured to remove the finished product from the granulation units (2), and
(iv) a control unit (12) configured to adjust process conditions within each granulation unit (2),
wherein the inlets (4) of all of the plurality of granulation units (2) are connected in parallel to the inlet line (19), and
wherein the outlets (5) of all of the plurality of granulation units (2) are connected in parallel to the outlet line (10).

2. The fluidized bed installation (1) as claimed in claim 1, further comprising a cleaning module (11), which is operatively connected with each granulation unit (2) and with which each granulation unit (2) may be cleaned independently of every other granulation unit (2).

3. The fluidized bed installation (1) as claimed in claim 2, characterized in that the cleaning module (11) is configured to carry out cleaning with manual intervention or cleaning without manual intervention.

4. The fluidized bed installation (1) as claimed in claim 1, further comprising at least one module inlet (13), wherein the at least one module inlet (13) connects the inlets (4) of all the granulation units (2) to the inlet line (19), and wherein the at least one module inlet (13) is drivable by the control unit (12).

5. The fluidized bed installation (1) as claimed in claim 4, wherein the at least one module inlet (13) takes the form of a central distribution module (18) and/or buffer module and/or changeover valve and/or switch and/or ring line.

6. The fluidized bed installation (1) as claimed in claim 1, further comprising at least one module outlet (14), wherein the at least one module outlet (14) connects the outlets (5) of all the granulation units (2) to the outlet line (10), and wherein the at least one module outlet (14) is drivable by the control unit (12).

7. The fluidized bed installation (1) as claimed in claim 1, characterized in that the at least one spray nozzle (8) is arranged in a bottom (15) and/or in a lid (16) and/or in a side wall (17) of the granulation unit (2).

8. The fluidized bed installation (1) as claimed in claim 1, further comprising a cleaning module (11), which is operatively connected with each granulation unit (2) and with which each granulation unit (2) may be cleaned independently of every other granulation unit (2).

9. The fluidized bed installation (1) as claimed in claim 8, characterized in that the cleaning module (11) is configured to carry out cleaning with manual intervention or cleaning without manual intervention.

10. The fluidized bed installation (1) as claimed in claim 9, further comprising at least one module inlet (13), wherein the at least one module inlet (13) connects the inlets (4) of all the granulation units (2) to the inlet line 19, and wherein the at least one module inlet (13) is drivable by the control unit (12).

11. The fluidized bed installation (1) as claimed in claim 10, wherein the at least one module inlet (13) takes the form of a central distribution module (18) and/or buffer module and/or changeover valve and/or switch and/or ring line.

12. The fluidized bed installation (1) as claimed in claim 11, further comprising at least one module outlet (14), wherein the at least one module outlet (14) connects the outlets (5) of all the granulation units (2) to the outlet line (10), and wherein the at least one module outlet (14) is drivable by the control unit (12).

13. The fluidized bed installation (1) as claimed in claim 12, characterized in that the at least one spray nozzle (8) is arranged in a bottom (15) and/or in a lid (16) and/or in a side wall (17) of the granulation unit (2).

14. A method for semi-continuous production of pharmaceutical granules, the method comprising providing a fluidized bed installation (1) as claimed in claim 1,
wherein the granulation units (2) of the fluidized bed installation (1) are operated and/or cleaned mutually independently.

* * * * *